(12) United States Patent
Bork (10) Patent No.: US 7,181,963 B2
(45) Date of Patent: Feb. 27, 2007

(54) THERMAL FLOW SENSOR HAVING STREAMLINED PACKAGING

(75) Inventor: Toralf Bork, Neuchatel (CH)

(73) Assignee: Codman & Shurtleff, Inc, Raynham, MA (US)

( * ) Notice: Subject to any disclaimer, the term of this patent is extended or adjusted under 35 U.S.C. 154(b) by 0 days.

(21) Appl. No.: 10/881,478

(22) Filed: Jun. 30, 2004

(65) Prior Publication Data
US 2006/0000271 A1   Jan. 5, 2006

(51) Int. Cl.
*G01F 1/68* (2006.01)
(52) U.S. Cl. .................................. 73/204.26
(58) Field of Classification Search ............ 73/204.26, 73/204.11, 204.22, 202.5
See application file for complete search history.

(56) References Cited

U.S. PATENT DOCUMENTS

| | | | | |
|---|---|---|---|---|
| 4,343,768 | A | * | 8/1982 | Kimura ...................... 422/97 |
| 4,542,650 | A | * | 9/1985 | Renken et al. ................ 73/196 |
| 4,555,940 | A | * | 12/1985 | Renger .................... 73/204.23 |
| 5,533,497 | A | * | 7/1996 | Ryder .................... 128/200.21 |
| 2002/0190839 | A1 | | 12/2002 | Padmanabhan |
| 2003/0049877 | A1 | | 3/2003 | Mayer |

FOREIGN PATENT DOCUMENTS

| | | |
|---|---|---|
| EP | 0689036 A | 12/1995 |
| EP | 1365216 A | 11/2003 |
| WO | WO 03/089885 A | 10/2003 |

OTHER PUBLICATIONS

European Search Report EP 05254056 dated Nov. 25, 2005.

* cited by examiner

*Primary Examiner*—Edward Lefkowitz
*Assistant Examiner*—Corey D. Mack (57) ABSTRACT

A thermal flow sensor has a first, second and third substrate, each having a first side and a second opposite side. The first substrate is connected to the second substrate such that the second side of the first substrate abuts the first side of the second substrate. The third substrate is connected to the second substrate such that the second side of the second substrate abuts the first side of the third substrate. The first, second and third substrate form a multi-layer body structure having at least one edge extending between a first side of the first substrate and the second side of the third substrate. The second substrate has a groove formed therein so as to form a conduit bounded by the second substrate and the second side of the first substrate and the first side of the third substrate. The conduit has an inlet opening and an outlet opening that are formed in the at least one edge.

29 Claims, 6 Drawing Sheets

THERMAL FLOW SENSOR HAVING STREAMLINED PACKAGING

BACKGROUND OF THE INVENTION

1. Field of the Invention

The present invention relates to a thermal flow sensor. More particularly, the present invention relates to a thermal flow sensor that can be used to monitor the flow of cerebrospinal fluid (CSF) within a shunt.

2. Discussion of Related Art

Hydrocephalus is a condition caused by an abnormal accumulation of CSF in cavities inside the brain. If not treated properly, hydrocephalus can cause severe disablements in children and adults, and can even cause death. If cerebrospinal fluid accumulates, the ventricles become enlarged and the pressure inside the brain increases. Hydrocephalus is a severe degenerative condition that occurs in children from birth on. Hydrocephalus is presumably caused by a complex interaction between genetic and environmental factors. A person can also acquire hydrocephalus later in life, which can be due to, for example, spina bifida, brain hemorrhage, meningitis, skull trauma, tumors and cysts.

Hydrocephalus occurs in newborns with a frequency of approximately 1 out of 5,000–10,000. There is currently no known prevention or cure for hydrocephalus. The most effective treatment so far is the surgical implantation of a shunt behind the ear. A shunt is a flexible tube that is inserted into the ventricular system of the brain to divert the cerebro fluid to other regions of the body. However, shunts frequently malfunction, leading to infections which can cause severe complications for the patient (e.g., delayed development, learning disabilities).

According to some estimates, up to 50% of patients who receive a shunt, will have the shunt malfunction at some time during his or her lifetime. Most shunt malfunctions are due to a blocked catheter and an incorrectly adjusted shunt valve.

The present inventors believe that the occurrence of complications due to a shunt malfunction can be detected easier by using a miniaturized implantable flow sensor, in accordance with the present invention, that has been developed for monitoring CSF flow. The sensor employs temperature sensors and a heater that do not contact the CSF, yet measures the CSF flow and can therefore be implanted so as to last for an extended period of time (e.g., greater than 10 years).

In particular, when a shunt valve is implanted in children, a malfunction of the implant can be effectively detected by use of an additional implanted sensor.

The thermal flow sensor in accordance with the present invention represents a significant advance in the treatment of hydrocephalus in patients and also represents an additional step towards the development of a closed-loop control system, which can continuously optimize the flow rate in the patient's shunt valve.

In addition, the thermal flow sensor of the present invention provides physicians with novel, previously unattainable information about the formation and drainage of cerebro spinal fluid (CSF).

SUMMARY OF THE INVENTION

In accordance with a currently preferred exemplary embodiment, the present invention involves athermal flow sensor having a first substrate having a first side and a second opposite side. A second substrate has a first side and a second opposite side. The first substrate is connected to the second substrate such that the second side of the first substrate abuts the first side of the second substrate. A third substrate has a first side and a second opposite side. The third substrate is connected to the second substrate such that the second side of the second substrate abuts the first side of the third substrate. The first, second and third substrate form a multi-layer body structure having at least one edge extending between a first side of the first substrate and the second side of the third substrate. The second substrate has a groove formed therein so as to form a conduit bounded by the second substrate and the second side of the first substrate and the first side of the third substrate. The conduit has an inlet opening and an outlet opening. Each of the openings are formed in the at least one edge.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE CURRENTLY PREFERRED EXEMPLARY EMBODIMENT

Figure 1:
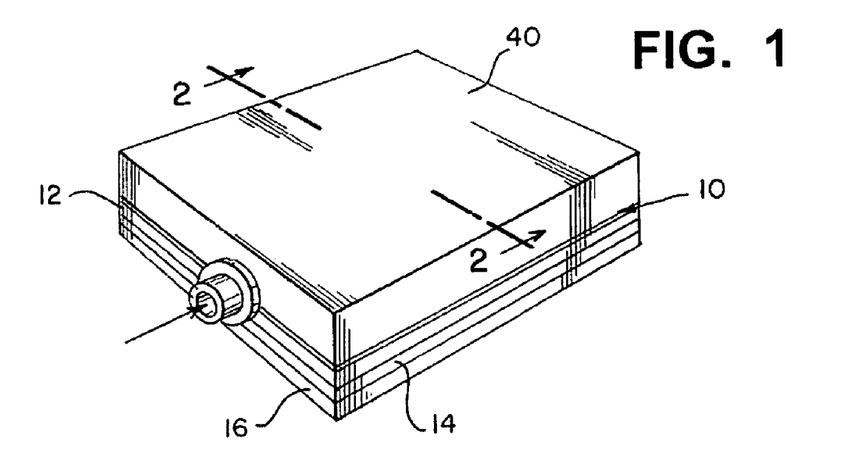
FIG. 1 is a perspective view of the thermal flow sensor in accordance with the present invention.
Figure 2:
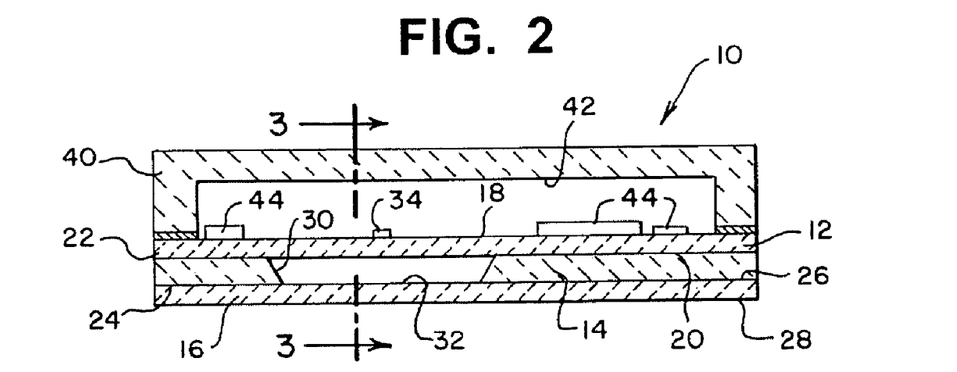
FIG. 2 is a cross-sectional schematic view taken along line 2—2 of FIG. 1 and looking in the direction of the arrows.

Referring now to FIGS. 1 though 6, a thermal flow sensor 10 in accordance with the present invention is illustrated. The thermal flow sensor in a currently preferred exemplary embodiment includes a first substrate 12, a second substrate 14 and a third substrate 16. First substrate 12 has a first side 18 and a second opposite side 20. Second substrate 14 has a first side 22 and a second opposite side 24. Third substrate 16 has a first side 26 and a second opposite side 28. First substrate 12 is connected to second substrate 14 such that the second side 20 of the first substrate 12 abuts the first side 22 of the second substrate 14. Third substrate 16 is connected to the second substrate 14 such that the second side 24 of the second substrate 14 abuts the first side 26 of the third substrate. The first substrate is preferably bonded to the second substrate, and the second substrate is preferably bonded to the third substrate. The first and third substrates are preferably made of borosilicate glass, for example PYREX® or BOROFLOAT®. The second substrate is preferably made of silicon.

Second substrate 14 has a groove 30 formed therein so as to form a conduit 32 bounded by the second substrate 14 and the second side 20 of the first substrate and the first side 26 of the third substrate, as illustrated in FIG. 1. The groove is preferably formed by etching into the silicon second substrate 14. In one exemplary embodiment, the groove may have a cross-sectional dimension of 380 µm×3000 µm. A heater 34 is disposed on the first side 18 of the first substrate 12 opposed to conduit 32. A first temperature sensor 36 is disposed on the first side 18 of said first substrate 12 opposed to conduit 32. A second temperature sensor 38 is also disposed on the first side 18 of the first substrate 12 opposed to conduit 32. This sensor can detect a temperature difference of approximately 0.005° C. at a flow rate of 300 ml/hr.

Figure 12:
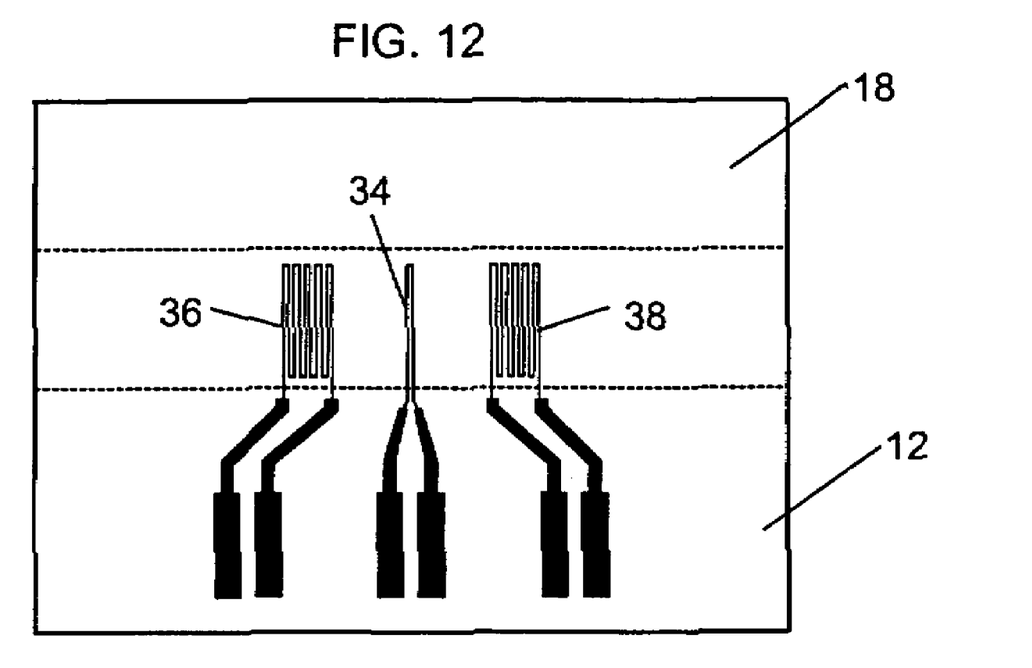
FIG. 12 is a schematic plan view of the first or second side of the first substrate showing the heater and temperature sensors.

The temperature sensors and heater are preferably created by metal deposition (e.g., evaporation or sputtering) directly on the first side or second side of the first substrate, which is preferably made of borosilicate glass. These metal deposition processes permit one to deposit thin films of metal on the glass surface within a vacuum chamber. A person skilled in the art will readily understand how to pattern the thin films by lithographic processes. In one exemplary embodiment, the metal thin film is made of several layers (e.g., Chromium (Cr), Platinum (Pt), Titanium (Ti) and Gold (Au)). Chromium or Titanium is preferably used as an adhesion layer since it sticks well to the borosilicate glass. Afterwards, a layer of Pt is deposited on the Cr or Ti so that it may be used as the heater and temperature structures. One may also at the same time as when the heater and temperature sensors are created, create the electrical tracks for the remainder of the electronics on the same substrate. A gold layer is preferably deposited on top of the platinum only in the region where there is no heater or temperature sensor structure and serves as the electrical tracks for the rest of the electronic circuit. However, in the region where there is no heater or temperature sensor, the gold layer could be deposited directly on the adhesion layer of Cr or Ti. The heater works by resistive heating by passing a current therethrough, as shown in FIG. 12. The temperature sensors work by having their resistance change due to its ambient temperature, as also shown in FIG. 12. In the present invention sensors, the ambient temperature at each temperature sensor is dependent upon among other things, the amount of heat created by the heater, the thickness of the first substrate, and the flow rate of the fluid flowing through the conduit.

A cap 40 is mounted on the first side 18 of the first substrate 12, thereby forming an interior chamber 42. Cap 40 is preferably made of PYREX® and is brazed to the first substrate, thereby forming a hermetically sealed interior chamber 42. When the sensor is used as an implantable medical device, a final parylene layer is applied on the outer surface of the sensor to prevent rejection of the implant by the body. Heater 34, first temperature sensor 36 and second temperature sensor 38 are disposed within interior chamber 42. Other electronics 44 are also disposed within chamber 42 and are electrically connected to heater 34, first temperature sensor 36 and second temperature sensor 38. One skilled in the art will readily know how to assemble the electronics so that data from the heater and/or sensors can be communicated by telemetry to and from an external control unit. By placing the temperature sensors and the heater on the opposite side of the first substrate from the conduit, the sensors and heater are not in direct contact with the fluid (e.g., CSF) within the conduit. This structure is referred to as an inverted substrate. Thus, the sensor in accordance with the present invention is a biocompatible design, which is favorable for long-term implants such as a hydrocephalus shunt, an infusion pump (e.g. >10 years). The biocompatible packaging of the sensor and the electronics has at least the following advantages:

The body fluid comes in contact only with biocompatible glass.

The Ti/Pt sensors, heater and sensor electronics are located on the same substrate, which reduces their manufacturing cost.

The sensor electronics can be drastically miniaturized by employing an ASIC, which can be fabricated by flip-chip technology.

Figure 3:
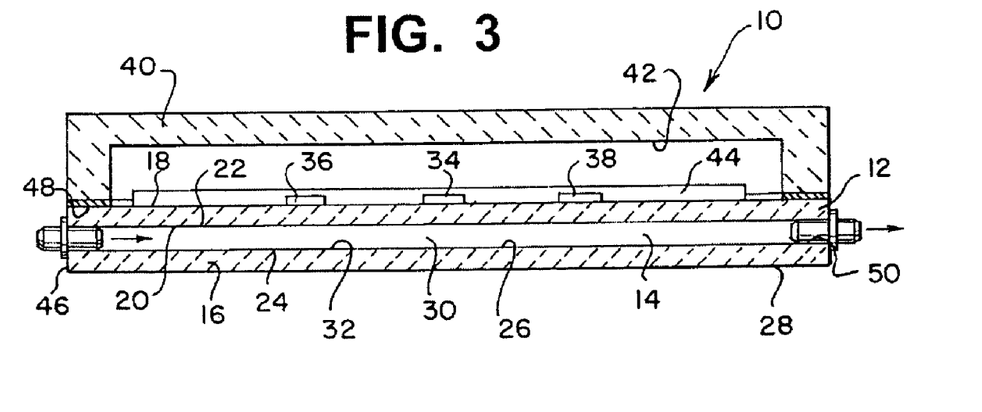
FIG. 3 is a cross-sectional view taken along line 3—3 of FIG. 2 and looking in the direction of the arrows.
Figure 4A:
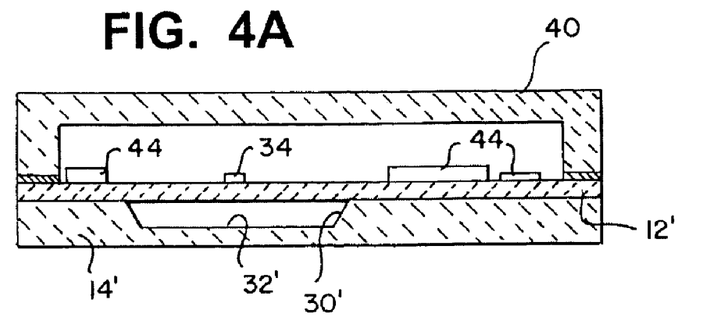
FIG. 4A is a cross-sectional view similar to FIG. 2 showing the thermal flow sensor having only two substrates with the groove formed in the second substrate.

In accordance with an alternative embodiment, the thermal flow sensor can comprise of two substrates 12' and 14', with a groove 30' formed within either substrate or both to form a conduit 32' bounded by both substrates, as illustrated in FIGS. 4a, b and c. In another alternative embodiment, the thermal flow sensor can comprise of only one substrate 12", as shown in FIGS. 5 and 6. Substrate 12" has a first upper side 18" and a second opposite lower side 20", and at least one side edge 46" extending between first upper side 18" and second lower side 20". A conduit 32" is formed within substrate 12". Conduit 12" has an inlet opening 48" and an outlet opening 50". Each of the openings 48", 50" are formed in the at least one edge 46", as shown in FIG. 3.

To determine the flow rate of a fluid flowing within conduit 32, 32', 32", fluid is permitted to flow through the conduit by entering into the inlet opening of the conduit and exiting from the exit opening. The fluid is heated with the heater 34 opposed to and remote from the conduit. In other words, the heater and temperature sensors are not in contact with the fluid flowing within the conduit. The temperature of the fluid is detected with the first temperature sensor disposed on the first side of the body opposed to and remote from the conduit. The temperature of the fluid may also be detected with the second temperature sensor disposed on the first side of the body opposed to and remote from the conduit. In a currently preferred exemplary embodiment, the two temperature sensors are spaced apart by about 2000 µm. The spacing between the temperature sensors is in part dependent upon the flow rate to be measured. Based on the detected temperature(s), the flow rate of the fluid can readily be determined by one skilled in the art. The fluid is preferably CSF, and thermal flow sensor 10 is preferably disposed within shunt 100, as shown in FIG. 10.

In designing the sensor in accordance with the present invention, the sensor was optimized through static and dynamic FEM simulations for flow ranges reaching 300 ml/hr, with optimized sensitivity at a flow range of 25 ml/hr, and for rapid step responses of 2 seconds. The normal flow range of CSF is about 25 ml/hr. At a flow range of 25 ml/hr, the sensitivity of the sensor signal is about 140 mV/ml/hr; and for high flow ranges of >270 ml/hr, the sensitivity of the sensor signal is still about 5 mV/ml/hr. The response time of the sensor of about 2 sec. is considerably reduced as compared to about 10 sec. for conventional sensors on a glass substrate. In addition, these conventional sensors can only detect flow rates up to 2–3 ml/hr. The fast step response makes it possible to measure CSF flow even when the patient's head position changes rapidly (e.g., when arising, or getting up from sleeping, etc.).

Referring now to FIG. 3, the first, second and third substrate together form a multi-layer body structure that has at least one edge 46 extending between the first side 18 of the first substrate and said second side 28 of the third substrate. Conduit 32 has an inlet opening 48 and an outlet opening 50, each of which are formed in the at least one edge 46. In a currently preferred exemplary embodiment, inlet opening 48 and outlet opening 50 are disposed solely in the second substrate 14. A dicing saw may be used to cut through the three layers to expose the openings in the second substrate. This embodiment is referred to as a streamline packaging because the inlet and outlet openings are in the side edges of the body structure as opposed to the top and/or bottom surface.

Figures 7, 8:
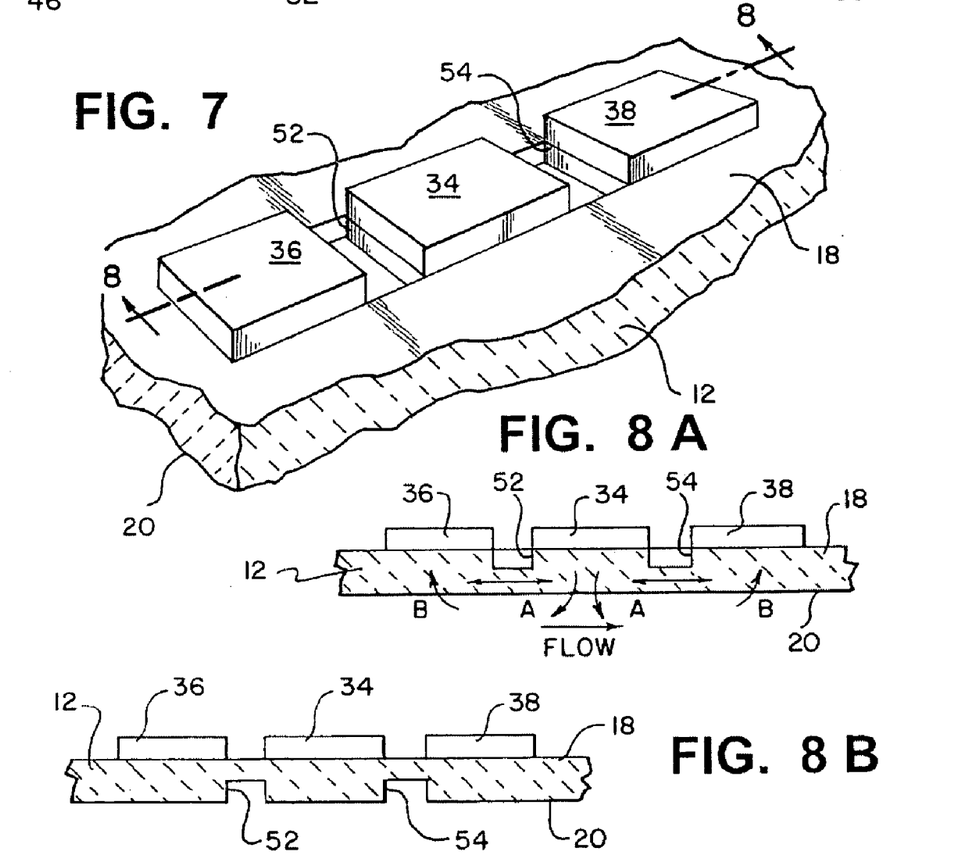
FIG. 7 is an enlarged partial perspective view of the first substrate and the heater and two temperature sensors mounted on the upper surface of the first substrate.
Figure 8:
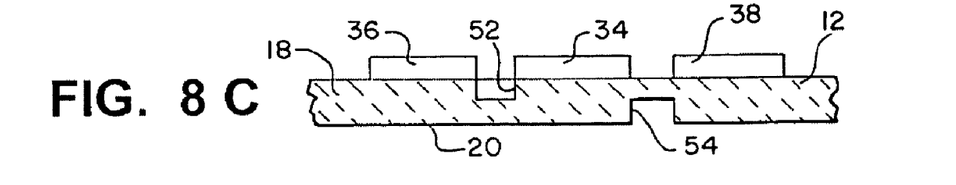
FIG. 8A is a partial cross-sectional view of the thermal flow sensor showing the recesses in the first side of the first substrate.
FIG. 8B is a partial cross-sectional view of the thermal flow sensor showing the recess in the second side of the first substrate.
FIG. 8C is a partial cross-sectional view of the thermal flow sensor showing one of the recesses on the first side of the first substrate and the other recess on the second side of the first substrate.
FIG. 8D is a partial cross-sectional view of the thermal flow sensor showing the recesses on the first side of the first substrate and on the second side of the first substrate.
Figure 8D:
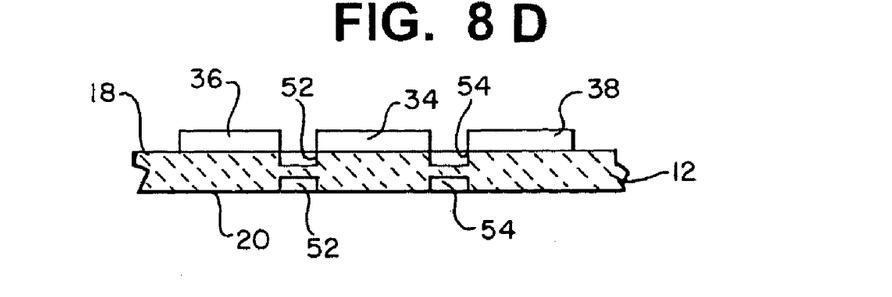

Referring now to FIG. 7, in accordance with another embodiment of the present invention, a first recess 52 is formed in the first side 18 of the first substrate 12 between heater 34 and the first temperature sensor 36. As shown, first recess 52 is disposed immediately adjacent to heater 34. A second recess 54 is formed in the first side 18 of the first substrate 12 between heater 34 and the second temperature sensor 38 (see FIG. 8A). As shown, second recess 54 is disposed immediately adjacent to heater 34 on an opposite side of the heater from the first recess. Alternatively, as shown in FIGS. 8B and 8C, the recesses 52, 54 can be formed in the second side of the first substrate 12 or one on one side of the first substrate and the other on the second side of the first substrate, respectively. Recesses 52, 54 preferably extend into the first substrate for about half of the thickness of the first substrate. In accordance with another variation of the present invention, the recesses 52, 54 can be disposed on the first side of the first substrate and on the second side of the first substrate.

The recesses 52, 54 are used to help guide the heat generated by heater 34 through the first substrate, as indicated by arrows A, and into conduit 32. The heat energy absorbed by the fluid is then transferred back through the first substrate, as indicated by arrows B, to the first and second temperature sensors. Because air is not a very good conductor of heat, most, if not effectively all, of the heat generated by the heater travels along the path indicated by arrows A and B. Of course, some heat will travel through the first substrate, but one of skill in the art will readily be able to calibrate the thermal flow sensor in accordance with the present invention to take this factor into account. Depending upon the thickness of the first substrate, how much heat is generated by the heater, the dimension of the recesses, and other factors known to those skilled in the art, one can readily determine the flow rate of the fluid flowing through the conduit. This information can then be transmitted by telemetry to an external control unit (not shown).

Figure 4B:
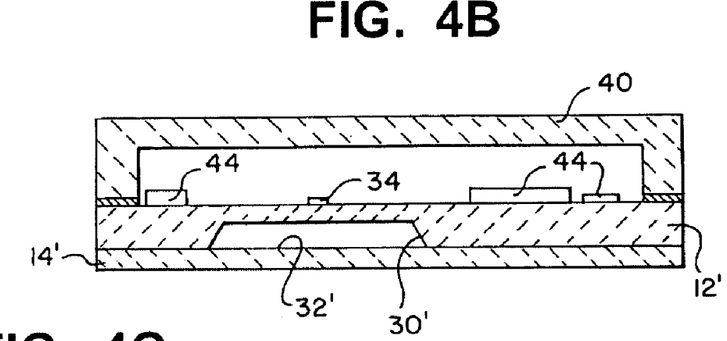
FIG. 4B is a cross-sectional view similar to FIG. 2 showing the thermal flow sensor having only two substrates with the groove formed in the first substrate.
Figure 4C:
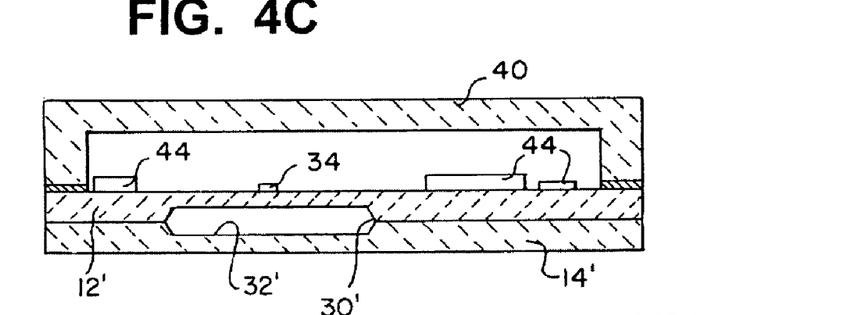
FIG. 4C is a cross-sectional view similar to FIG. 2 showing the thermal flow sensor having only two substrates with the groove formed in both the first and second substrate.
Figure 5:
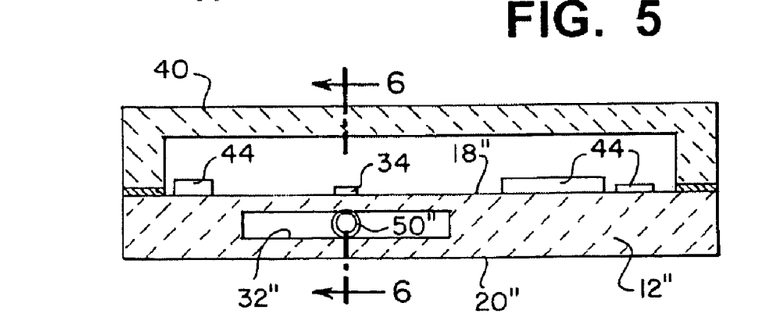
FIG. 5 is a cross-sectional view similar to FIG. 2 showing the thermal flow sensor having only one substrate with the groove formed therein.
Figure 6:
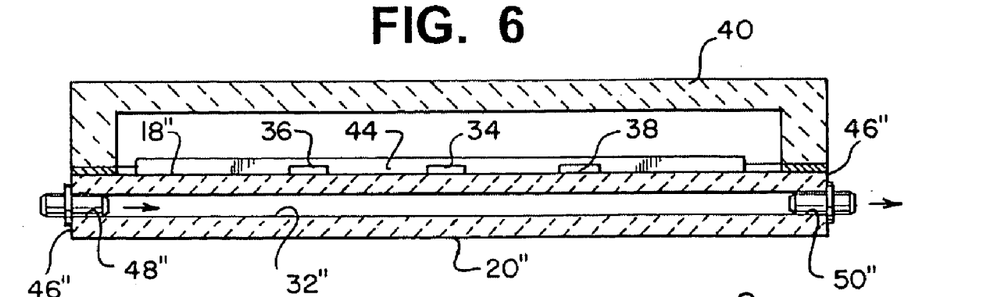
FIG. 6 is a cross-sectional view taken along line 6—6 of FIG. 5 and looking in the direction of the arrows.

As in the previous alternative embodiments shown in FIGS. 4A–5, the thermal flow sensor having recesses 52, 54 can also be comprised of two substrates 12' and 14', as illustrated in FIGS. 4a, b and c, or with only one substrate 12", as shown in FIG. 5.

Figure 9A:
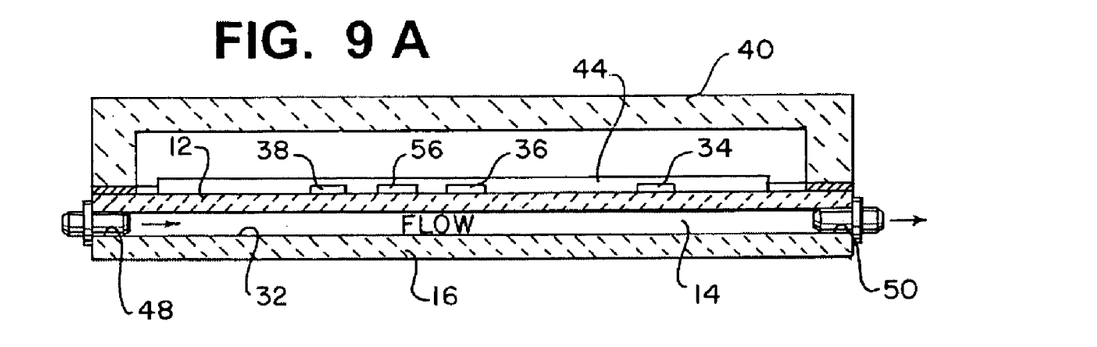
FIG. 9A is a cross-sectional view of the thermal flow sensor showing an asymmetric design of the temperature sensors upstream from the heater.

Referring now to FIG. 9A, a thermal flow sensor in accordance with yet another embodiment of the present invention is illustrated. In this embodiment, first temperature sensor 36 is disposed on the first side of the first substrate opposed to the conduit and at a first predetermined distance from heater 34 in a direction opposite to the fluid flow direction within the conduit. Second temperature sensor 38 is disposed on the first side of the first substrate opposed to the conduit and at a second predetermined distance from heater 34 in a direction opposite to the fluid flow direction. As illustrated in FIG. 9A, the second predetermined distance is greater than the first predetermined distance. This embodiment is referred to as an asymmetric sensor design because both temperature sensors are disposed on one side of the heater, as opposed to having the heater being disposed between the two temperature sensors with respect to the flow direction.

Figure 9B:
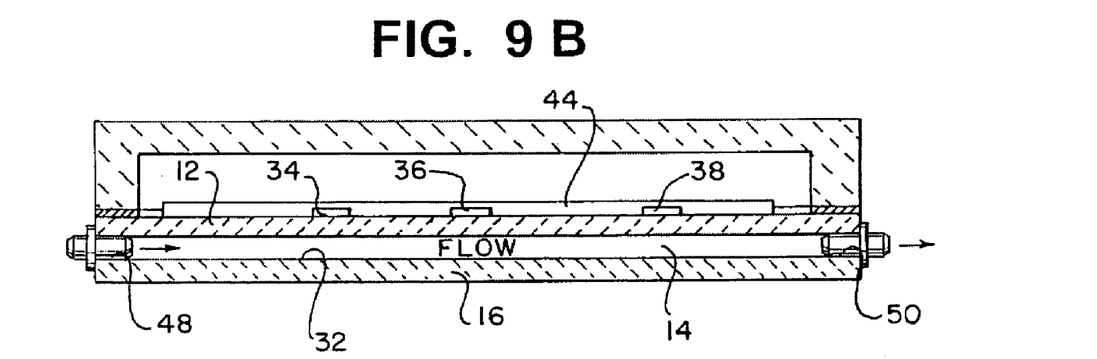
FIG. 9B is a cross-sectional view of the thermal flow sensor showing an asymmetric design of the temperature sensors downstream from the heater.

Referring now to FIG. 9B, a variation of the embodiment of FIG. 9 is illustrated. In this variation, the first and second temperature sensors are disposed at a respective first and second predetermined distance from the heater in the fluid flow direction, as opposed to opposite to the fluid flow direction.

Figure 10:
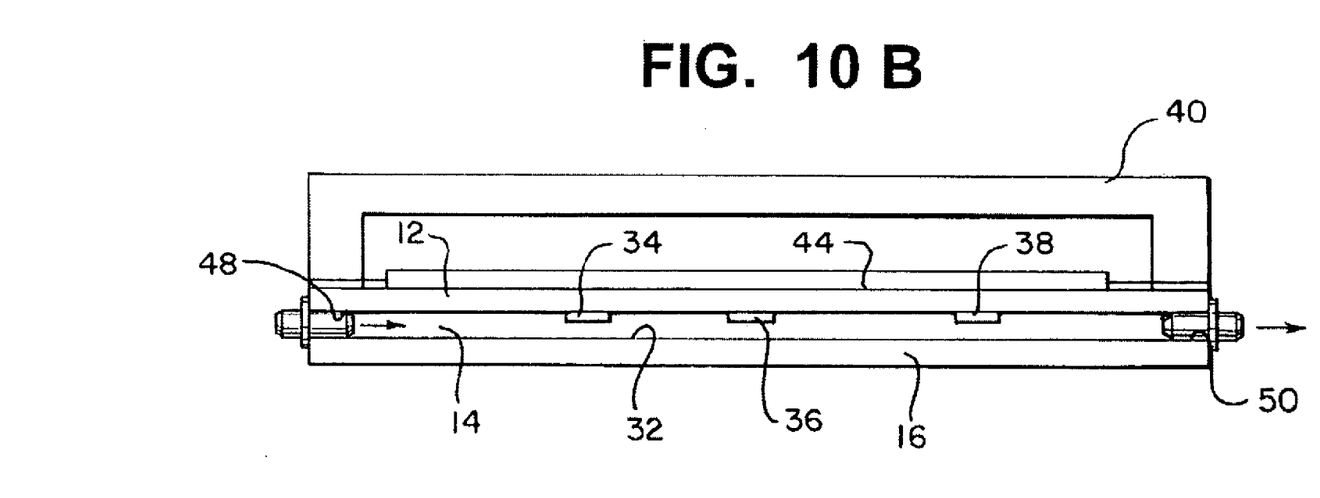
FIG. 10A is a cross-sectional view of the thermal flow sensor showing an asymmetric design of the temperature sensors upstream from the heater and within the conduit.
FIG. 10B is a cross-sectional view of the thermal flow sensor showing an asymmetric design of the temperature sensors downstream from the heater and within the conduit.
Figure 10A:
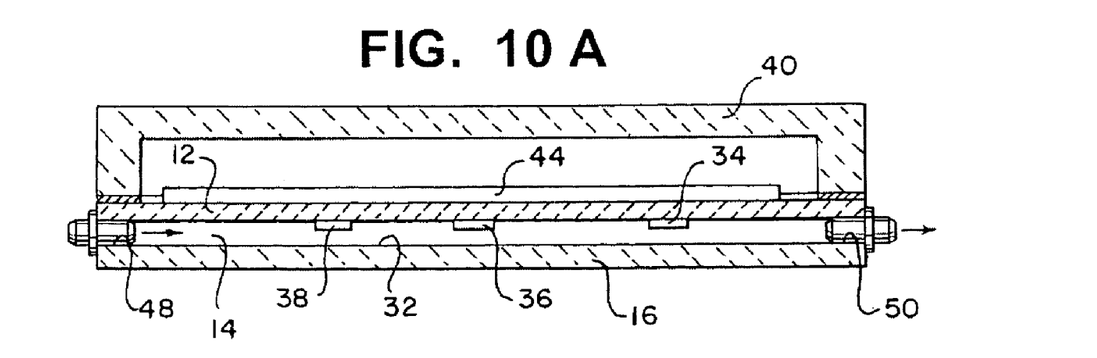
Figure 11:
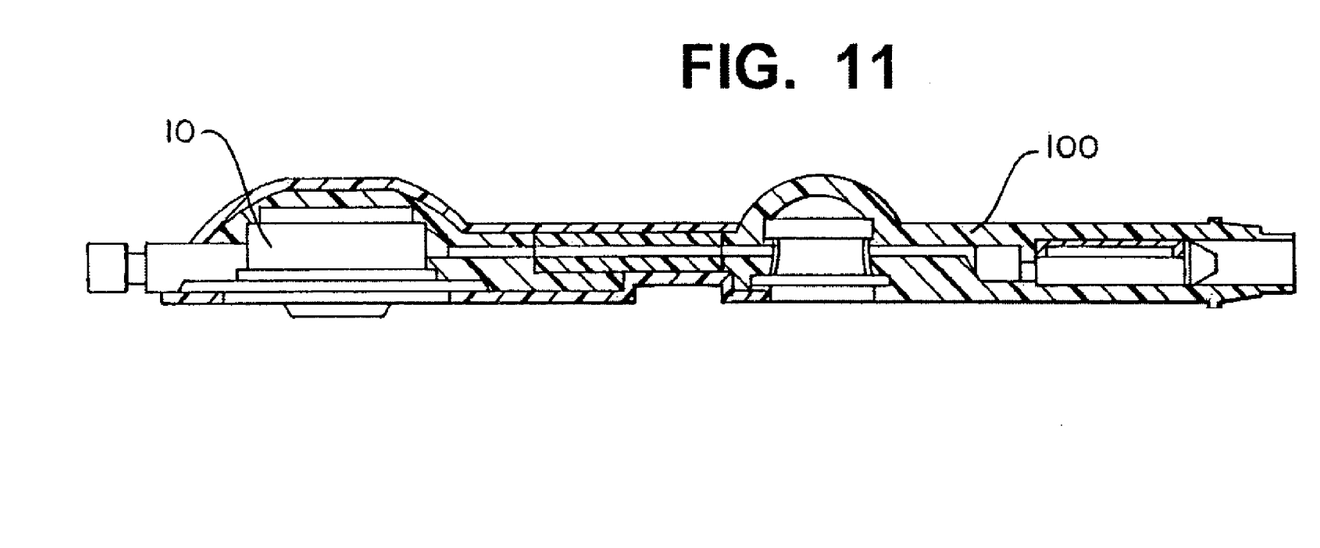
FIG. 11 is a perspective view showing the thermal flow sensor being incorporated within a shunt.

Referring now to FIGS. 10A and 10B, another variation of the embodiment of FIG. 9 is illustrated. In accordance with this variation, the heater and the temperature sensors are disposed within the conduit and, therefore, in contact with the fluid flowing within the conduit. In accordance with this variation the first and second temperature sensors are disposed at a respective first and second predetermined distance from the heater just as in the FIG. 9A embodiment opposite to the fluid flow direction as shown in FIG. 10, or as in the FIG. 9B embodiment in the fluid flow direction, as shown in FIG. 10.

As in the previous alternative embodiments shown in FIGS. 4A–5, the thermal flow sensor, which has the first and second temperature sensors disposed on the same side of the heater, either opposite to the flow direction or in the flow direction, can also be comprised of two substrates 12' and 14', as illustrated in FIGS. 4a, b and c, or with only one substrate 12", as shown in FIG. 5.

The present inventors have discovered that the asymmetric sensor design can not detect flow below a certain flow rate that will be referred to as the cut-off flow rate. The cut-off flow rate is typically about 1 to 2 ml/hr. To detect flow from 0 ml/hr up to the cut-off rate, one may use a second heater 56, as illustrated in FIG. 9A. Heater 56 is disposed between second sensor 38 and first sensor 36 with respect to the flow direction.

Having described the presently preferred exemplary embodiment of a thermal flow sensor in accordance with the present invention, it is believed that other modifications, variations and changes will be suggested to those skilled in the art in view of the teachings set forth herein. Substitutions of elements from one described embodiment to another are also fully intended and contemplated. It is also to be understood that the drawings are not necessarily drawn to scale, but that they are merely conceptual in nature. It is, therefore, to be understood that all such modifications, variations, and changes are believed to fall within the scope of the present invention as defined by the appended claims.

Every issued patent, pending patent application, publication, journal article, book or any other reference cited herein is each incorporated by reference in their entirety.

What is claimed is:

1. A thermal flow sensor comprising;
   a first substrate having a first side and a second opposite side;
   a second substrate having a first side and a second opposite side, said first substrate being connected to said second substrate such that said second side of said first substrate abuts said first side of said second substrate;
   a third substrate having a first side and a second opposite side, said third substrate being connected to said second substrate such that said second side of said second substrate abuts said first side of said third substrate; and
   wherein said first, second and third substrate forming a multi-layer body structure having at least one edge extending between a first side of said first substrate and said second side of said third substrate; said second substrate having a groove formed therein so as to form a conduit bounded by said second substrate and second side of said first substrate and first side of said third substrate, said conduit having an inlet opening and an outlet opening, each of said openings being formed in said at least one edge.

2. The thermal flow sensor according to claim 1, wherein said inlet opening is disposed solely in said second substrate.

3. The thermal flow sensor according to claim 2, wherein said outlet opening is disposed solely in said second substrate.

4. The thermal flow sensor according to claim 1, further comprising:
   a heater disposed on said first side of said first substrate opposed to said conduit; and
   a first temperature sensor disposed on said first side of said first substrate opposed to said conduit.

5. The thermal flow sensor according to claim 1, further comprising:
   a second temperature sensor disposed on said first side of said first substrate opposed to said conduit.

6. The thermal flow sensor according to claim 5, further comprising a cap mounted on said first side of said first substrate thereby forming an interior chamber, said heater, said first temperature sensor and said second temperature sensor being disposed within said interior chamber.

7. The thermal flow sensor according to claim 6, wherein said cap is brazed to said first substrate thereby forming a sealed interior chamber.

8. The thermal flow sensor according to claim 7, further comprising electronics within said chamber and electrically connected to said heater, said first temperature sensor and said second temperature sensor to permit said electronics to communicate by telemetry to a control unit.

9. The thermal flow sensor according to claim 1, wherein said first and third substrate are made of borosilicate glass.

10. The thermal flow sensor according to claim 9, wherein said second substrate is made of silicon.

11. The thermal flow sensor according to claim 1, wherein said first substrate is bonded to said second substrate and said second substrate is bonded to said third substrate.

12. A thermal flow sensor comprising:
    a first substrate having a first side and a second opposite side;
    a second substrate having a first side and a second opposite side, said first substrate being connected to said second substrate such that said second side of said first substrate abuts said first side of said second substrate;
    wherein said first and second substrate forming a multi-layer body structure having at least one edge extending between a first side of said first substrate and said second side of said second substrate; at least one of said first substrate and said second substrate having a groove formed therein so as to form a conduit bounded by said first and second substrates, said conduit having an inlet opening and an outlet opening, each of said openings being formed in said at least one edge of said multi-layer body structure; further comprising:
    a heater disposed on said first side of said first substrate opposed to said conduit; and
    a first temperature sensor disposed on said first side of said first substrate opposed to said conduit.

13. The thermal flow sensor according to claim 12, wherein said inlet opening is disposed solely in said second substrate.

14. The thermal flow sensor according to claim 13, wherein said outlet opening is disposed solely in said second substrate.

15. The thermal flow sensor according to claim 12, further comprising:
    a second temperature sensor disposed on said first side of said first substrate opposed to said conduit.

16. The thermal flow sensor according to claim 15, further comprising a cap mounted on said first side of said first substrate thereby forming an interior chamber, said heater, said first temperature sensor and said second temperature sensor being disposed within said interior chamber.

17. The thermal flow sensor according to claim 16, wherein said cap is brazed to said first substrate thereby forming a sealed interior chamber.

18. The thermal flow sensor according to claim 17, further comprising electronics within said chamber and electrically connected to said heater, said first temperature sensor and said second temperature sensor to permit said electronics to communicate by telemetry to a control unit.

19. The thermal flow sensor according to claim 12, wherein said first substrate is made of borosilicate glass.

20. The thermal flow sensor according to claim 19, wherein said second substrate is made of silicon.

21. The thermal flow sensor according to claim 12, wherein said first substrate is bonded to said second substrate.

22. A thermal flow sensor comprising:
    a first substrate having a first upper side and a second opposite lower side, and at least one side edge extending between said first upper side and said second lower side, a conduit formed therein having an inlet opening and an outlet opening, each of said openings being formed in said at least one edge;

a heater disposed on said first side off said first substrate opposed to said conduit; and a first temperature sensor disposed on said first side of said first substrate opposed to said conduit.

23. The thermal flow sensor according to claim 22, further comprising:

a second temperature sensor disposed on said first side of said first substrate opposed to said conduit.

24. The thermal flow sensor according to claim 23, further comprising a cap mounted on said first side of said first substrate thereby forming an interior chamber, said heater, said first temperature sensor and said second temperature sensor being disposed within said interior chamber.

25. The thermal flow sensor according to claim 24, wherein said cap is brazed to said first substrate thereby forming a sealed interior chamber.

26. The thermal flow sensor according to claim 25, further comprising electronics within said chamber and electrically connected to said heater, said first temperature sensor and said second temperature sensor to permit said electronics to communicate by telemetry to a control unit.

27. A method of determining the flow rate of a fluid within a conduit within a body, said body having a first upper side and a second opposite lower side, and at least one side edge extending between said first upper side and said second lower side, a conduit formed within the body having an inlet opening and an outlet opening, each of said openings being formed in said at least one side edge, said method comprising the steps of:

permitting a fluid to enter into the inlet opening of the conduit;

heating the fluid with a heater disposed on the first side of the body opposed to and remote from the conduit;

detecting a temperature of the fluid with a first temperature sensor disposed on the first side of the body opposed to and remote from the conduit;

permitting the fluid to exit from exit opening of the conduit;

determining the flow rate of the fluid based on the detected temperature;

disposing the heater on said first side of said first substrate opposed to said conduit; and disposing the first temperature sensor on said first side of said first substrate opposed to said conduit.

28. The method according to claim 27, wherein said fluid is a liquid.

29. The method according to claim 27, wherein said liquid is cerebro spinal fluid.

* * * * *